US011052135B2

(12) United States Patent
Okuyama et al.

(10) Patent No.: US 11,052,135 B2
(45) Date of Patent: Jul. 6, 2021

(54) METHODS AND COMPOSITIONS FOR TREATING HUNTER SYNDROME

(71) Applicants: GREEN CROSS CORPORATION, Yongin-si (KR); MediGeneBio Corporation, Yongin-si (KR)

(72) Inventors: Torayuki Okuyama, Tokyo (JP); Thong-Gyu Jin, Seoul (KR); Han-Yeul Byun, Yongin-si (KR); Jin-Wook Seo, Yongin-si (KR); Byoung-Ju Lee, Yongin-si (KR); Yong-Chul Kim, Yongin-si (KR); In-Young Jang, Yongin-si (KR); Kyuhyun Lee, Yongin-si (KR)

(73) Assignees: GREEN CROSS CORPORATION, Yongin (KR); MEDIGENEBIO CORPORATION, Yongin (KR)

( * ) Notice: Subject to any disclaimer, the term of this patent is extended or adjusted under 35 U.S.C. 154(b) by 256 days.

(21) Appl. No.: 16/066,187

(22) PCT Filed: Dec. 21, 2016

(86) PCT No.: PCT/KR2016/015060
§ 371 (c)(1),
(2) Date: Jun. 26, 2018

(87) PCT Pub. No.: WO2017/116066
PCT Pub. Date: Jul. 6, 2017

(65) Prior Publication Data
US 2020/0268857 A1 Aug. 27, 2020

Related U.S. Application Data

(60) Provisional application No. 62/369,970, filed on Aug. 2, 2016, provisional application No. 62/272,843, filed on Dec. 30, 2015.

(51) Int. Cl.
*A61P 3/00* (2006.01)
*A61K 38/46* (2006.01)
*A61K 9/00* (2006.01)
*A61K 47/26* (2006.01)

(52) U.S. Cl.
CPC .......... *A61K 38/465* (2013.01); *A61K 9/0019* (2013.01); *A61K 9/0085* (2013.01); *A61K 47/26* (2013.01); *A61P 3/00* (2018.01); *C12Y 301/06013* (2013.01)

(58) Field of Classification Search
CPC combination set(s) only.
See application file for complete search history.

(56) References Cited

U.S. PATENT DOCUMENTS

| 6,153,188 | A | 11/2000 | Wilson et al. |
| 6,537,785 | B1 | 3/2003 | Canfield |
| 9,220,677 | B2 * | 12/2015 | Zhu ............... C12Y 310/01001 |
| 10,456,454 | B2 | 10/2019 | Calias et al. |
| 2011/0318323 | A1 | 12/2011 | Zhu et al. |
| 2014/0271598 | A1 * | 9/2014 | Zhu ........................ A61P 25/08 424/94.3 |
| 2015/0320843 | A1 | 11/2015 | Jin et al. |

FOREIGN PATENT DOCUMENTS

| JP | 2012-62312 A | 3/2012 |
| JP | 2013-530989 A | 8/2013 |
| MX | 2013000321 A | 4/2013 |
| RU | 2599848 C2 | 10/2016 |
| WO | 2011/163648 A1 | 12/2011 |
| WO | 2012/108828 A1 | 8/2012 |
| WO | 2013096912 A2 | 6/2013 |
| WO | 2013/148277 A1 | 10/2013 |

OTHER PUBLICATIONS

Sohn, Y.B., Cho, S.Y., Park, S.W. et al. Phase I/II clinical trial of enzyme replacement therapy with idursulfase beta in patients with mucopolysaccharidosis II (Hunter Syndrome). 2013, Orphanet J Rare Dis 8, 42.). (Year: 2013).*
Japanese Patent Office, Communication dated May 28, 2019, issued in Application No. 2018-534600.
Pericles Calias et al., "CNS Penetration of Intrathecal-Lumber Idursulfase in the Monkey, Dog and Mouse: Implications for Neurological Outcomes of Lysosomal Storage Disorder", PLoS One, 2012, vol. 7, No. 1.
International Search Report PCT/KR2016/015060 dated Mar. 27, 2017.

\* cited by examiner

*Primary Examiner* — Heidi Reese
(74) *Attorney, Agent, or Firm* — Sughrue Mion, PLLC

(57) ABSTRACT

The present invention provides, among other things, compositions and methods for CNS delivery of Idursulfase-beta, a human recombinant iduronate-2-sulfatase protein, for effective treatment of Hunter Syndrome. The compositions and methods provided by the present invention effectively reduce symptoms not only in brain and spinal cord but also in peripheral tissues including heart, liver, spleen, lung, and kidney.

17 Claims, 5 Drawing Sheets
Specification includes a Sequence Listing.

SEQUENCE LISTING

```
<160> NUMBER OF SEQ ID NOS: 2

<210> SEQ ID NO 1
<211> LENGTH: 525
<212> TYPE: PRT
<213> ORGANISM: Artificial
<220> FEATURE:
<223> OTHER INFORMATION: Recombinant IDS-beta protein

<400> SEQUENCE: 1

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
```

-continued

```
                245                 250                 255
Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
            275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
    515                 520                 525
```

<210> SEQ ID NO 2
<211> LENGTH: 525
<212> TYPE: PRT
<213> ORGANISM: Artificial
<220> FEATURE:
<223> OTHER INFORMATION: Recombinant IDS-beta protein (Cysteine at
    position 59 is post-translationally modified to Formylglycine)
<220> FEATURE:
<221> NAME/KEY: MOD_RES
<222> LOCATION: (59)
<223> OTHER INFORMATION: FORMYLATION (Position 59 is Formylglycine)

<400> SEQUENCE: 2

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Gly Ala Pro Ser Arg Val
    50                  55                  60
```

```
Ser Phe Leu Thr Gly Arg Arg Pro Asp Thr Thr Arg Leu Tyr Asp Phe
 65                  70                  75                  80

Asn Ser Tyr Trp Arg Val His Ala Gly Asn Phe Ser Thr Ile Pro Gln
                 85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480
```

-continued

```
Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525
```

METHODS AND COMPOSITIONS FOR TREATING HUNTER SYNDROME

CROSS REFERENCE TO RELATED APPLICATIONS

This application is a National Stage of International Application No. PCT/KR2016/015060 filed Dec. 21, 2016, claiming priority based on U.S. Provisional Application Nos. 62/272,843 filed Dec. 30, 2015 and 62/369,970 filed Aug. 2, 2016.

TECHNICAL FIELD

This invention is directed to an improved methods and compositions for treating hunter syndrome.

BACKGROUND ART

Mucopolysaccharidosis type II (MPS II, Hunter syndrome) is an X-linked recessively inherited lysosomal storage disorder caused by a deficiency of iduronate-2-sulfatase, which functions to degrade mucopolysaccharides [1]. Deficiency of iduronate-2-sulfatase results in the accumulation of undegraded glycosaminoglycans (GAGs) in the cells and leads to progressive multi-organ damage [2]. Among the various types of GAGs, dermatan sulfate (DS) and heparan sulfate (HS) are the principal accumulating GAGs in MPS II [2].

The clinical phenotype of MPS II is classified into attenuated and severe forms. Patients with the attenuated form show somatic manifestations, including coarse face, hepatosplenomegaly, dysostosis multiplex, and joint stiffness without neurological involvement, while patients with the severe form have neurological impairment and progressive neurodegeneration in addition to the somatic symptoms. An insufficient level of endogenous IDS causes a pathological buildup of heparan sulfate and dermatan sulfate in, e.g., the heart, liver, central nervous system (CNS), etc. Symptoms including neurodegeneration and mental retardation appear during childhood; and early death can occur due to organ damage in the brain.

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency.

As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

Many have believed that the barrier to diffusion at the brain's surface, as well as the lack of effective and convenient delivery methods, were too great an obstacle to achieve adequate therapeutic effect in the brain for any disease. Hunter Syndrome affects the nervous system and thus demonstrates unique challenges in treating these diseases with traditional therapies. There is often a large build-up of glycosaminoglycans (GAGs) in neurons and meninges of affected individuals, leading to various forms of CNS symptoms.

Thus, there remains a great need to effectively deliver therapeutic agents to the brain. More particularly, there is a great need for more effective delivery of active agents to the central nervous system for the treatment of lysosomal storage disorders such as Hunter Syndrome.

To overcome the BBB, direct drug delivery via intrathecal or intraventricular injections of recombinant enzyme has demonstrated promising results in several types of MPS animal models [3-7]. Moreover, a phase I/II clinical trial reported that the intrathecal (IT) injection of idursulfase (IDS) reduced GAG concentrations in cerebrospinal fluid (CSF) by approximately 8090% in children with the severe form of MPS II. But, a large number of adverse events have been reported in the clinical trial, most of adverse events were related to the malfunction of IT drug delivery device [8].

Although the cellular mechanism of neurodegeneration in the severe form of MPS II is not completely understood, several recent studies have demonstrated a correlation between HS-derived disaccharides and mental retardation in large cohorts of MPS patients [9, 10]. In addition, animal studies have demonstrated that the HS possibly results in the neurological disorders associated with the MPS III mice model by activating integrin-based focal adhesion in astrocytes or neural stem cells [11, 12]. Akiyama et al. [13] reported that "the pathologic GAG" measured by the Sensi-Pro Non-Reducing End HS assay [14] had higher sensitivity and specificity than total GAGs in the brain tissue of MPS II mice [13]. Based on these data, the amount of accumulated HS could be a more sensitive biomarker for representing brain pathology and neurological function of MPS II than total GAG amount. However, measuring brain tissue HS is not possible in the clinical setting. Therefore, a useful clinical biomarker representing brain tissue HS needs to be discovered. We hypothesized that HS concentration in CSF could be one of the clinical biomarkers if it is correlated with the amount of brain tissue GAGs, especially HS.

A single ICV (intracerebroventricular) injection of IDS-β according to this invention was well tolerated, and it produced a significant reduction of HS and GAGs in the brain and other somatic tissues. We also discovered that a significant positive correlation of HS content in the CSF between brain HS and brain GAGs suggests that CSF HS concentration could be a useful biomarker for representing brain pathology in MPS patients with CNS involvement.

The present invention provides an effective approach for direct delivery of therapeutic agents to the central nervous system (CNS). The present invention is based on the discovery that Idursulfase-beta (IDS-β), a human recombinant Iduronate-2-sulfatase protein developed as an effective replacement enzyme for Hunter Syndrome, can be directly introduced into the ventricles of a subject through intracerebroventricular (ICV) administration, such that the enzyme effectively and extensively diffuses across various surfaces and penetrates various regions across the brain, including deep brain regions. The present inventors have demonstrated that such protein delivery can be achieved using simple saline-based formulations and without inducing substantial adverse effects, such as severe immune response, in the subject. Therefore, the present invention provides a highly efficient, clinically desirable and patient-friendly approach for direct CNS delivery for the treatment of Hunter Syndrome.

DISCLOSURE

Technical Problem

For the treatment of Hunter Syndrome, there remains a great need to effectively deliver therapeutic agents to the brain. Intrathecal (IT) injection, or the administration of therapeutic proteins to the cerebrospinal fluid (CSF), has recently been attempted to treat patients with Hunter Syndrome but a large number of adverse events have been reported in a clinical trial [8]. Although most of adverse events were related to the malfunction of IT drug delivery device, another approach such as intracerebroventricular (ICV) administration would be needed for the treatment of patients with Hunter Syndrome. ICV administration would be an effective approach for direct delivery of therapeutic agents to the ventricles of patients, there are no currently approved products and/or products under development for the treatment of Hunter Syndrome by ICV administration.

Technical Solution

1. A method of treating Hunter Syndrome comprising a step of administering intracerebroventricularly (ICV administration) to a subject in need of treatment a therapeutically effective dose of an ICV formulation comprising Idursulfase-beta (IDS-β) protein at a concentration ranging from approximately 0.1 mg/ml to approximately 60 mg/ml, Sodium chloride at a concentration of approximately 150 mM, polysorbate 20 at a concentration of approximately 0.05 mg/ml, and a pH of approximately 6.

2. The method of said technical solution 1, wherein said ICV formulation comprises Idursulfase-beta (IDS-β) protein at a concentration of approximately 15 mg/ml, Sodium chloride at a concentration of approximately 150 mM, polysorbate 20 at a concentration of approximately 0.05 mg/ml, and a pH of approximately 6.

3. The method of said technical solution 1, wherein said therapeutically effective dose is ranging from approximately 1 mg to approximately 30 mg.

4. The method of said technical solution 1, wherein said therapeutically effective dose is approximately 10 mg.

5. The method of said technical solution 1, wherein said ICV administration is performed once every three weeks.

6. The method of said technical solution 1, wherein said ICV administration is performed once every month.

7. The method of said technical solution 1, wherein said ICV administration is through an intraventricular catheter system comprising a reservoir and a catheter connected to said reservoir.

8. The method of said technical solution 7, further comprising steps of surgically implanting said intraventricular catheter system, wherein said reservoir is placed between the scalp and the brain of the subject in need of treatment and the end of said catheter is placed inside the ventricle of said subject such that the inner space of said reservoir is connected to the inner space of said ventricle through the inner space of said catheter so that cerebrospinal fluid flows from said ventricle into said reservoir to fill said reservoir; drawing out 0.1-5 ml of cerebrospinal fluid from said reservoir at a flow rate of 0.1-60 ml/minute; injecting 0.1-5 ml of said ICV formulation into said reservoir at a flow rate of 0.1-60 ml/minute; and allowing said ICV formulation to flow from said reservoir through said catheter into said ventricle.

9. The method of said technical solution 1, wherein said ICV administration is performed in combination with at least one additional form of enzyme replacement therapy treatment for Hunter Syndrome.

10. The method of said technical solution 9, wherein said additional form of enzyme replacement therapy treatment for Hunter Syndrome is selected from a group consisting of intravenous administration and subcutaneous administration.

11. The method of said technical solution 10, wherein said ICV administration is performed once every month and said intravenous administration is performed once every week.

12. The method of said technical solution 10, wherein said ICV administration is performed once every three weeks and said intravenous administration is performed once every week.

13. The method of said technical solution 10, wherein said ICV administration is performed once every month and said subcutaneous administration is performed once every week.

14. The method of said technical solution 10, wherein said ICV administration is performed once every three weeks and said subcutaneous administration is performed once every week.

15. The method of said technical solution 10, wherein said ICV administration is performed once every month and said subcutaneous administration is performed twice every week.

16. The method of said technical solution 10, wherein said ICV administration is performed once every three weeks and said subcutaneous administration is performed twice every week.

17. The method of said technical solution 10, wherein said ICV administration is performed once every month and said intravenous administration and said subcutaneous administration are performed alternatively at an interval of one week.

18. The method of said technical solution 10, wherein said ICV administration is performed once every three weeks and said intravenous administration and said subcutaneous administration are performed alternatively at an interval of one week.

19. A formulation for intracerebroventricular administration for treating Hunter Syndrome comprising Idursulfase-beta (IDS-β) protein at a concentration ranging from approximately 0.1 mg/ml to approximately 60 mg/ml, Sodium chloride at a concentration of approximately 150 mM, polysorbate 20 at a concentration of approximately 0.05 mg/ml, and a pH of approximately 6.

Advantageous Effects

Intracerebroventricular administered IDS-β according to this invention decreased heparan sulfate (HS) and glycosaminoglycans (GAGs) levels in brain and cerebrospinal fluid (CSF) in MPS II mice.

Intracerebroventricular administered IDS-β according to this invention decreased heparan sulfate (HS) and glycosaminoglycans (GAGs) levels in somatic (peripheral) tissues including heart, lung, liver, spleen and kidney in MPS II mice.

According to this invention, a tendency of GAG concentration in the brains can be predicted from heparan sulfate level in CSF, which can allow safer and easier diagnosis of severity of brain GAG accumulation.

BEST MODE

Figure 1:
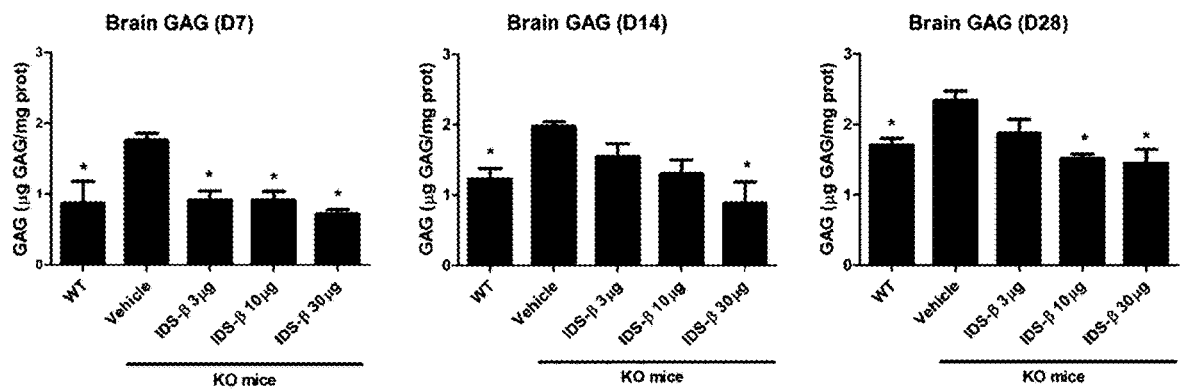
FIG. 1 shows GAGs levels in brain tissues of IDS KO mice after single ICV injection of IDS-β.

As described in detail below, the present inventors have successfully developed stable formulations for effective intracerebroventricular (ICV) administration of Idursulfase-beta (IDS-β) protein.

In various embodiments, the present invention includes a stable formulation for direct intracerebroventricular (ICV) administration comprising Idursulfase-beta (IDS-β) protein, salt, and a polysorbate surfactant. In some embodiments, the IDS-β protein is present in the ICV formulation at a concentration ranging from approximately 0.1-60 mg/ml (e.g., 0.1-60 mg/ml, 0.1-30 mg/ml, 0.3-30 mg/ml, 0.2-20 mg/ml, 0.2-6 mg/ml, 0.6-6 mg/ml, 5-60 mg/ml, or 10-60 mg/ml). In some embodiments, the IDS-β protein is present in the ICV formulation at or up to a concentration selected from 0.1 mg/ml, 0.2 mg/ml, 0.5 mg/ml, 0.6 mg/ml, 1 mg/ml, 2 mg/ml, 5 mg/ml, 6 mg/ml, 10 mg/ml, 15 mg/ml, 20 mg/ml, 30 mg/ml, 40 mg/ml, 50 mg/ml, 55 mg/ml, or 60 mg/ml.

In various embodiments, the present invention includes a stable formulation of any of the embodiments described herein. In some embodiments, IDS-β comprises proteins having an amino acid sequence of SEQ ID NO:1. In some embodiments, IDS-β further comprises proteins having an amino acid sequence of SEQ ID NO:2. SEQ ID NO:1 is a recombinant human Iduronate-2-sulfatase protein. SEQ ID NO:2 is a recombinant human Iduronate-2-sulfatase protein with its 59th Cysteine replaced by a Formyl-Glycine (G*).

In some embodiments, IDS-β contains approximately 35% (mol percentage) or less of proteins having SEQ ID NO:1 and approximately 65% (mol percentage) or more of proteins having SEQ ID NO:2. In some embodiments, IDS-β contains approximately 20-35% (mol percentage) of proteins having SEQ ID NO:1 and approximately 65-80% (mol percentage) of proteins having SEQ ID NO:2.

In some embodiments, the IDS-β comprises proteins having an amino acid sequence at least 60%, 65%, 70%, 75%, 80%, 85%, 90%, 95%, or 98% identical to SEQ ID NO:1. In some embodiments, the IDS-β comprises proteins having an amino acid sequence at least 60%, 65%, 70%, 75%, 80%, 85%, 90%, 95%, or 98% identical to SEQ ID NO:2.

In some embodiments, the stable formulation of any of the embodiments described herein includes a salt. In some embodiments, the salt is Sodium chloride (NaCl). In some embodiments, the NaCl is present at a concentration ranging from approximately 0-300 mM (e.g., 0-250 mM, 0-200 mM, 0-150 mM, 50-250 mM, or 100-200 mM). In some embodiments, the NaCl is present at a concentration ranging from approximately 125-175 mM. In some embodiments, the NaCl is present at a concentration of approximately 150 mM.

In various embodiments, the present invention includes a stable formulation of any of the embodiments described herein, wherein the polysorbate surfactant is selected from the group consisting of polysorbate 20, polysorbate 40, polysorbate 60, polysorbate 80 and combination thereof. In some embodiments, the polysorbate surfactant is polysorbate 20 (Tween 20). In some embodiments, the polysorbate 20 is present at a concentration ranging approximately 0-0.02% (0-0.2 mg/ml). In some embodiments, the polysorbate 20 is present at a concentration of approximately 0.005% (0.05 mg/ml).

In various embodiments, the present invention includes a stable formulation of any of the embodiments described herein, wherein the formulation further comprises a buffering agent. In some embodiments, the buffering agent is selected from the group consisting of phosphate, acetate, histidine, succinate, Tris, and combinations thereof. In some embodiments, the buffering agent is phosphate. In some embodiments, the phosphate is present at a concentration no greater than 50 mM (e.g., no greater than 45 mM, 40 mM, 35 mM, 30 mM, 25 mM, 20 mM, 15 mM, 10 mM, 5 mM, 0.25 mM, or 0.12 mM). In some embodiments, the phosphate is present at a concentration no greater than 20 mM. In various aspects the invention includes a stable formulation of any of the embodiments described herein, wherein the formulation has a pH of approximately 3-8 (e.g., approximately 4-7.5, 5-8, 5-7.5, 5-6.5, 5-7.0, 5.5-8.0, 5.5-7.7, 5.5-6.5, 6-7.5, or 6-7.0). In some embodiments, the formulation has a pH of approximately 5.5-6.5 (e.g., 5.5, 6.0, 6.1, 6.2, 6.3, 6.4, or 6.5). In some embodiments, the formulation has a pH of approximately 6.0.

In various embodiments, the present invention includes stable formulations of any of the embodiments described herein, wherein the formulation is a liquid formulation. In various embodiments, the present invention includes stable formulation of any of the embodiments described herein, wherein the formulation is formulated as lyophilized dry powder.

In some embodiments, the present invention includes a stable formulation for ICV administration comprising IDS-β protein at a concentration ranging from approximately 0.1-60 mg/ml, NaCl at a concentration of approximately 150 mM, polysorbate 20 at a concentration of approximately 0.005% (0.05 mg/ml), and a pH of approximately 6.0. In some embodiments, the IDS-β protein is at a concentration of approximately 0.1 mg/ml, 0.2 mg/ml, 0.5 mg/ml, 0.6 mg/ml, 1 mg/ml, 2 mg/ml, 5 mg/ml, 6 mg/ml, 10 mg/ml, 15 mg/ml, 20 mg/ml, 30 mg/ml, 40 mg/ml, 50 mg/ml, 55 mg/ml, or 60 mg/ml.

In various aspects, the present invention includes a container comprising a single dosage form of a stable formulation in various embodiments described herein. In some embodiments, the container is selected from an ampule, a vial, a bottle, a cartridge, a reservoir, a lyo-ject, or a pre-filled syringe. In some embodiments, the container is a pre-filled syringe. In some embodiments, the pre-filled syringe is selected from borosilicate glass syringes with baked silicone coating, borosilicate glass syringes with sprayed silicone, or plastic resin syringes without silicone. In some embodiments, the stable formulation is present in a volume of less than about 50 mL (e.g., less than about 45 ml, 40 ml, 35 ml, 30 ml, 25 ml, 20 ml, 15 ml, 10 ml, 5 ml, 4 ml, 3 ml, 2.5 ml, 2.0 ml, 1.5 ml, 1.0 ml, or 0.5 ml). In some embodiments, the stable formulation is present in a volume of about 6.0 ml. In some embodiments, the stable formulation is present in a volume of about 3.0 ml. In some embodiments, 2.0 ml of stable formulation is present in a 6.0 ml vial. In some embodiments, 1.5 ml of stable formulation is present in a 5.0 ml vial. In some embodiments, 1.0 ml of stable formulation is present in a 3.0 ml vial.

In various aspects, the present invention includes methods of treating Hunters Syndrome including the step of administering intracerebroventricularly to a subject in need of treatment a formulation according to any of the embodiments described herein.

In some embodiments, the present invention includes a method of treating Hunter Syndrome including a step of administering intracerebroventricularly to a subject in need of treatment a formulation comprising IDS-β protein at a concentration ranging from approximately 0.1-60 mg/ml, NaCl at a concentration of approximately 150 mM, polysorbate 20 at a concentration of approximately 0.005% (0.05 mg/ml), and a pH of approximately 6.

In some embodiments, a subject in need of treatment has an intraventricular catheter system having a reservoir and a catheter, such as Ommaya reservoir, implanted for ICV administration. In some embodiments, ICV administration is performed by injecting the aforementioned ICV formulations at a flow rate of 0.1-60 ml/minute, into the reservoir. In some embodiments, the cerebrospinal fluid (CSF) of a subject is drawn out at a flow rate of 0.1-60 ml/minute, from the reservoir before ICV administration of the formulations, so that there is no net increase in the CSF volume of the subject after ICV administration, to prevent pressure increase in the brain. In some embodiments, the formulation injected into the reservoir is allowed to travel through the catheter into the ventricle of a subject by gently pressing and releasing the reservoir.

In some embodiments, the ICV administration results in no substantial adverse effects (e.g., severe immune response) in the subject. In some embodiments, the ICV administration results in no substantial adaptive T cell-mediated immune response in the subject.

In some embodiments, the ICV administration of the formulation results in delivery of the IDS-β protein to various target tissues in the brain, the spinal cord, and peripheral organs. In some embodiments, the ICV administration of the formulation results in delivery of the IDS-β protein to brain target tissues. In some embodiments, the brain target tissues comprise white matter and/or neurons in the gray matter. In some embodiments, the IDS-β protein is delivered to neurons, glial cells, perivascular cells and/or meningeal cells. In some embodiments, the IDS-β protein is further delivered to the neurons in the spinal cord.

In some embodiments, the ICV administration of the formulation further results in systemic delivery of the IDS-β protein to peripheral target tissues. In some embodiments, the peripheral target tissues are selected from, but not limited to, heart, liver, spleen, lung, and/or kidney.

In some embodiments, the ICV administration of the formulation results in cellular lysosomal localization in brain target tissues, spinal cord neurons and/or peripheral target tissues. In some embodiments, the ICV administration of the formulation results in reduction of GAG storage in brain target tissues, spinal cord neurons and/or peripheral target tissues. In some embodiments, the GAG storage is reduced by at least 10%, 20%, 30%, 40%, 50%, 60%, 70%, 80%, 90%, 1-fold, 1.5-fold, or 2-fold as compared to a negative control (e.g., GAG storage in the subject before treatment or after vehicle-only administration). In some embodiments, the ICV administration of the formulation results in reduced vacuolization in neurons (e.g., by at least 20%, 40%, 50%, 60%, 80%, 90%, 1-fold, 1.5-fold, or 2-fold as compared to a negative control). In some embodiments, the neurons comprise Purkinje cells.

In some embodiments, the ICV administration of the formulation results in increased IDS-β enzymatic activity in brain target tissues, spinal cord neurons and/or peripheral target tissues. In some embodiments, the IDS-β enzymatic activity is increased by at least 1-fold, 2-fold, 3-fold, 4-fold, 5-fold, 6-fold, 7-fold, 8-fold, 9-fold or 10-fold as compared to a negative control (e.g., endogenous enzymatic activity in the subject before treatment or after vehicle-only administration). In some embodiments, the increased IDS-β enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg.

In some embodiments, the ICV administration of the formulation results in reduced intensity, severity, or frequency, or delayed onset of at least one symptom or feature of the Hunter Syndrome. In some embodiments, the at least one symptom or feature of the Hunters Syndrome is cognitive impairment; white matter lesions; dilated perivascular spaces in the brain parenchyma, ganglia, corpus callosum, and/or brainstem; atrophy; and/or ventriculomegaly.

In some embodiments, the ICV administration takes place once every two weeks. In some embodiments, the ICV administration takes place once every three weeks. In some embodiments, the ICV administration takes place once every month. In some embodiments, the ICV administration takes place once every two months. In some embodiments, the administration is continuous, such as through a continuous perfusion pump. In some embodiments, the ICV administration is used in conjunction with intravenous (IV) administration. In some embodiments, the IV administration takes place once every week. In some embodiments, the IV administration takes place once every two weeks. In some embodiments, the IV administration takes place once every month. In some embodiments, the IV administration takes place once every two months.

In some embodiments, IV and ICV administrations are performed on the same day. In some embodiments, the IV and ICV administrations are not performed within a certain amount of time of each other, such as not within at least 2 days, within at least 3 days, within at least 4 days, within at least 5 days, within at least 6 days, within at least 7 days, or within at least one week. In some embodiments, IV and ICV administrations are performed on an alternating schedule, such as alternating administrations weekly, every other week, twice monthly, or monthly. In some embodiments, an ICV administration replaces an IV administration in an administration schedule, such as in a schedule of IV administration weekly, every other week, twice monthly, or monthly, every third or fourth or fifth administration in that schedule can be replaced with an ICV administration in place of an IV administration.

In some embodiments, IV and ICV administrations are performed sequentially, such as performing IV administrations first (e.g., weekly, every other week, once every three weeks, twice monthly, or monthly dosing for two weeks, a month, two months, three months, four months, five months, six months, a year or more) followed by ICV administrations (e.g., weekly, every other week, once every three weeks, twice monthly, or monthly dosing for more than two weeks, a month, two months, three months, four months, five months, six months, a year or more). In some embodiments, ICV administrations are performed first (e.g., weekly, every other week, once every three weeks, twice monthly, monthly, once every two months, once every three months dosing for two weeks, a month, two months, three months, four months, five months, six months, a year or more) followed by IV administrations (e.g., weekly, every other week, once every three weeks, twice monthly, or monthly dosing for more than two weeks, a month, two months, three months, four months, five months, six months, a year or more).

In some embodiments, the ICV administration is used in absence of IV administration.

In some embodiments, the ICV administration is used in absence of concurrent immunosuppressive therapy.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

1-1: Overview

This study was performed to investigate the pharmacological effect and doseresponse relationship of a single intracerebroventricular (ICV) injection of idursulfase beta (IDS-β) in MPS II mice. In addition, we measured the HS concentration in the CSF and investigated the correlation between the CSF HS and brain tissue HS and GAGs of MPS II mice.

Three doses of ICV IDS-β injections (3, 10, and 30 µg) were performed, and the tissue GAGs (brain, heart, lung, liver, spleen, and kidney) were measured at 7, 14, and 28 days after injection. HS was measured by using LC/MS-MS in the CSF and brains of mice. The total GAGs in the brain and other somatic tissues of all the IDS-β-treated groups were significantly reduced. The significant reduction was maintained for 28 days in the 30-µg injection group. We also demonstrated that HS content was reduced in both the CSF and brain tissue of all IDS-β-treated groups. Furthermore, we demonstrated that HS concentration in the CSF was significantly correlated with brain HS and brain tissue GAGs.

A single ICV injection of IDS-β according to this invention was well tolerated, and it produced a significant reduction of HS and GAGs in the brain and other somatic tissues. We also discovered that a significant positive correlation of HS content in the CSF between brain HS and brain GAGs suggests that CSF HS concentration could be a useful biomarker for representing brain pathology in MPS II patients with CNS involvement.

1-2: Methods

Animals

We used the previously reported IDS knockout (KO) mice. Briefly, the Ids gene was deleted from exon 2 to exon 3 [15]. The IDS KO mice were bred from a C57BL/6.129S background strain and had a null mutation in the Ids gene. The wild-type (WT) control mice were bred from a C57BL/B6.129S strain. The genotype of all mice was confirmed by a polymerase chain reaction of DNA obtained from a tail snip. This study was approved by the Institutional Animal Care and Use Committee (Approval No. 20140925005) and performed in accordance with the animal welfare policy of Samsung Biomedical Research Institute, Seoul, Korea.

Study Design

The 6-week-old animals were allocated to five groups (12 animals in each group) by stratified randomization. IDS KO mice were allocated to four groups: IDS KO mice with vehicle injection and IDS KO mice with three different doses (3 µg, 10 µg, and 30 µg) of IDS-β (Green Cross Corp., Yongin, Korea) injection. Four animals in each group were sacrificed every 7, 14, and 28 days after the ICV injection. The GAG concentrations of various tissues (brain, heart, lung, liver, spleen, and kidney) were analyzed, and HS concentrations from the CSF and brain were measured on 7, 14, and 28 days after injection.

Preparation of IDS-β for ICV Injection

The vehicle solution was 150 mM sodium chloride 0.05 mg/mL Tween 20 solution (Merck Millipore, Darmstadt, Germany). The concentrated IDS-β (50 mg/mL) drug solutions were diluted with the vehicle to make concentrations of 0.6, 2, and 6 mg/mL.

ICV Injection

Figure 5A:
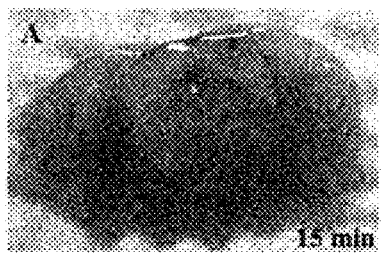
FIGS. 5(A) through 5(C) show brain tissues harvested at different time points after injection and visualized with trypan blue.
Figure 5B:
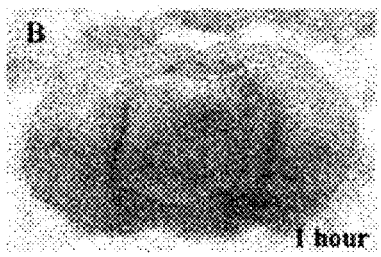
Figure 5C:
Figure 6:
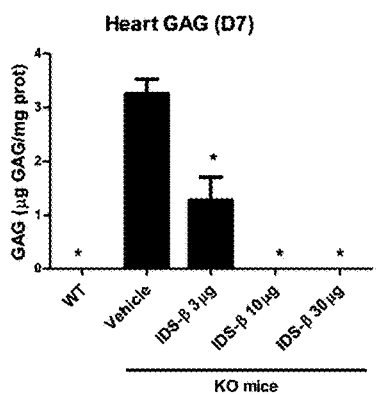
FIG. 6 shows GAGs levels in heart tissues of IDS KO mice after single ICV injection of IDS-β.
Figure 6:
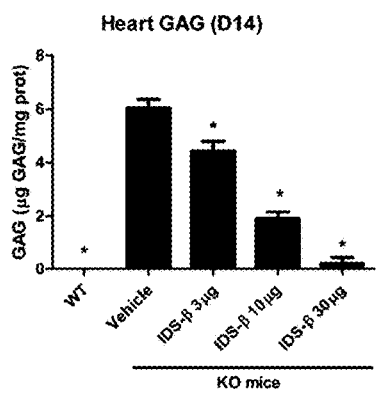
Figure 6:
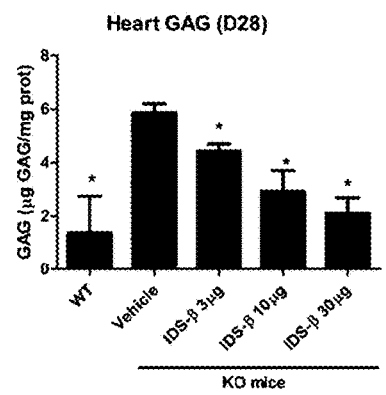
Figure 7:
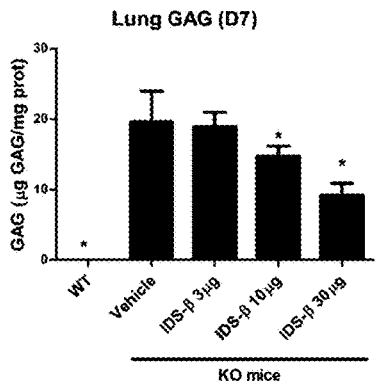
FIG. 7 shows GAGs levels in lung tissues of IDS KO mice after single ICV injection of IDS-β.
Figure 7:
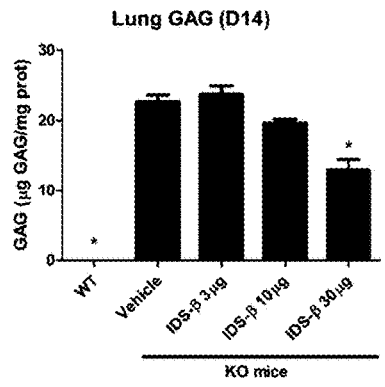
Figure 7:
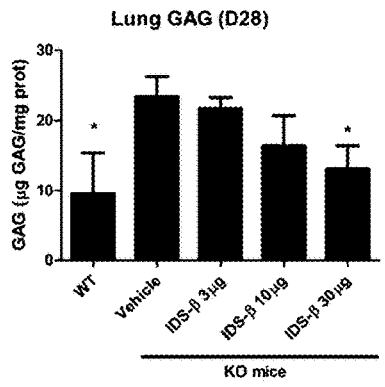
Figure 8:
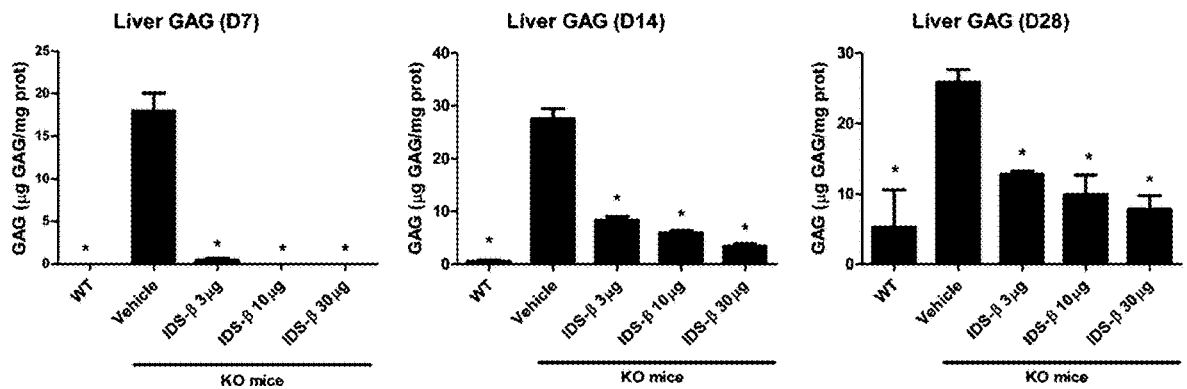
FIG. 8 shows GAGs levels in liver tissues of IDS KO mice after single ICV injection of IDS-β.
Figure 9:
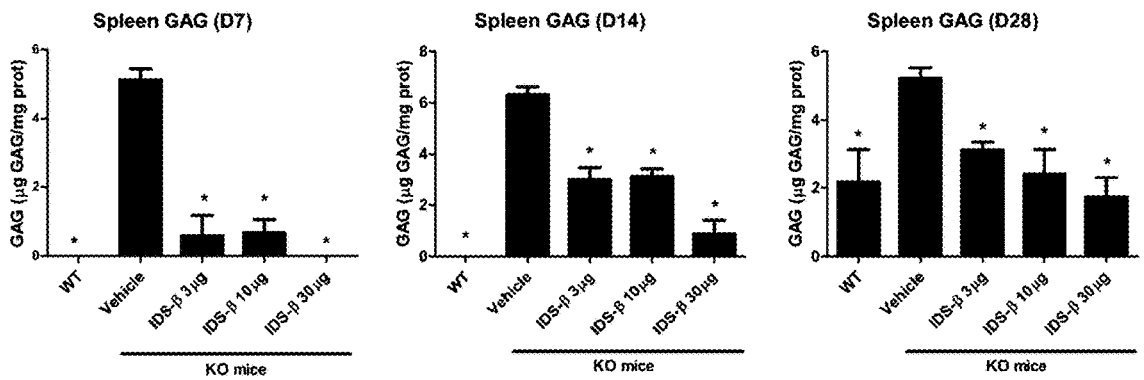
FIG. 9 shows GAGs levels in spleen tissues of IDS KO mice after single ICV injection of IDS-β.
Figure 10:
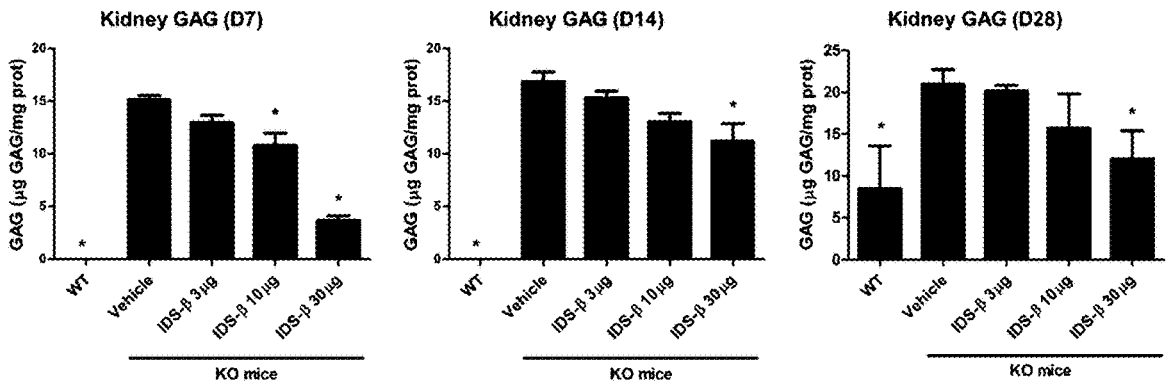
FIG. 10 shows GAGs levels in kidney tissues of IDS KO mice after single ICV injection of IDS-β.

The single ICV injection of the mice was done at 6 weeks of age. Each drug solution or vehicle was administered ICV to mice in a total volume of 5 µL. On the dosing day, mice were anesthetized with isoflurane (Hana Pharm., Korea) inhalation and placed in a stereotactic instrument. After making a small incision, the skull was exposed and cleaned. The ICV injection was performed according to the modified methods reported previously [16, 17]. The IDS-β or vehicle, was injected into the right lateral ventricle with a 31-gauge needle at a rate of 10 mL/minute controlled by a syringe pump (Harvard Apparatus, Holliston, Mass., USA) using the coordinates (Benchmark, Neurolab, St. Louis, Mo.): 0.58 mm caudal to bregma, 1.25 mm lateral to sagittal suture, and 1.77 mm in depth. The injection site was monitored for ruptured vessels or facial swelling. And then the needle was removed 15 seconds after discontinuation of plunger movement to prevent backflow. The incision was closed with wound clips and the mice were placed on an isothermal pad at 37° C. and observed following surgery until recovery. The entire protocol took 10-15 minutes for one animal. To demonstrate the successful ICV injection technique, the dye solution was ICV injected. The brain was harvested at different time points post-injection and visualized. Proper injection of one of the ventricles allowed distribution of the trypan blue (0.05%) on the injected side of the brain approximately 10-15 minutes post-injection. A wide distribution of trypan blue in cerebral hemisphere was visible approximately 1 hour—post injection. Inaccurate injections can be distinguished by lack of blue color in cerebral hemisphere (FIG. 5).

CSF and Tissue Collection

At 7, 14, and 28 days after the injection, the mice were euthanized by the injection of excessive amounts of Alfaxalone (Jurox/name: Alfaxan) solution (15 mg/kg). The CSF was collected from the cisterna magna by borosilicate glass (O.D.: 10 mm, I.D.:0.75 mm) and frozen for HS concentration measurement. The blood in the mice brain tissue was cleaned by transcardiac perfusion with phosphate-buffered saline (PBS) for 1520 min. The brain tissue was collected and frozen on dry ice. Then, the samples were homogenized and divided into quarters (half was used for GAG measurement and half for HS measurement). The other somatic tissues (heart, lung, liver, spleen, and kidney) were also collected and homogenized in PBS.

Measurement of Total GAG Concentration in Tissues

The homogenized tissue samples were shaken overnight at 4° C. and centrifuged for 15 min at 12,000×g, and then the supernatants were collected. Total GAG levels were measured using the sGAG Assay kit (Kamiya Biochemicals, Japan). First, 50 μL of homogenized samples were incubated with 50 μL of 8 mol/L Guanidine-HCl at room temperature (RT) for 15 min. Then, 50 μl of STA solution (0.3% H2SO4, 0.75% Triton X-100) was added for 15 min at RT, and a solution of alcian blue was added to the solution for 15 min. The samples were then centrifuged for 15 min at 12,000 rpm and rinsed with DMSO solution (40% DMSO, 0.05 mol/L MgCl2). Finally, 500 μL of Gu-prop solution (4 mol/L Guanidine-HCl, 33% 1-propanol, 0.25% Triton X-100) was added to the pellets, and the mix was allowed to dissolve completely. Alternatively, absorbance was read in the X-Mark (Bio-Rad, Hercules, Calif.) at 600 nm. The GAG concentration was normalized to the protein concentration, which was measured with a BCA Protein Assay kit (ThermoFisher, Waltham, Mass.). The GAG concentration was expressed as g of GAG/mg of protein, as calculated through the standard curve of the GAG substrate, chondroitin sulfate-6. The data of each sample was the average of duplicate measurements.

Measurement of HS in CSF and Brain Tissue

HS levels in the mouse CSF and brain tissue samples were determined using LC-MS/MS. 5 mg/mL of the each calibration standards (STD) stock solutions were prepared by dissolving HS sodium salt or DS in water. The STD stock solutions were diluted with an appropriate volume of water to prepare 0.1, 0.2, 0.5, 1.0, 2.0, 5.0, 10 and 20 μg/mL of STD and 0.2, 2 and 15 μg/mL of quality control (QC) samples. Also, 5 mg/mL of STD stock solutions were deuterium-labeled to make HS-d6 and DS-d6 as internal standard (IS). 20 μL of STD solutions were added to a glass test tube and evaporated under nitrogen. The residue was methanolyzed by mixing with 200 μL of methanol-d4-acetyl chloride (400:64, v/v) and heating for 90 min at 65° C. After methanolysis, the solvent was evaporated under nitrogen. The residue was reconstituted in 1 mL of water, diluted with Water-methanol-formic acid (950:50:1, v/v/v: Buffer A) and the prepared solution was used as IS stock solution. Mouse CSF sample was centrifuged at 2100×g at 4° C. for 5 min and the supernatant was diluted with an equal volume of PBS. Mouse brain tissue was homogenized with 0.01 mol/L of sodium hydroxide (50 or 100 times of volume for brain weight). The homogenate was incubated for 24 hours at room temperature and 20 μL of homogenate was added to 180 μL of Water-chloroform (4:5, v/v). After mixing, the sample was centrifuged at 10000×g at 4° C. for 5 min and the supernatant was diluted with an equal volume of PBS. These samples prepared from CSF and brain were used as test samples for analysis of LC-MS/MS. 4 μL of test sample from CSF (20 μL from brain), STD or QC in test tube was evaporated under nitrogen. To the residue was added 50 μL of 3M HCl-MeOH and 5 μL of 2,2-dimethoxy propane and was sonicated for 3 min, heated for 90 min at 65° C. and evaporated. The residue was reconstituted with 200 μL of IS stock solution, sonicated for 3 min and was transferred to a centrifugal filter, centrifuged at 10000×g at 4° C. for 3 min, and the resultant filtrate was analyzed. 5 μL of each samples was injected into triple quadrupole mass spectrometer API5000 (AB/MDS Sciex) equipped with an ACQUITY UPLC system (Waters). Test sample and IS were separated on an ACQUITY UPLC HSS T3 column (100 A 1.8 μm, 2.1 mm by 100 mm) heated at 40° C. The initial mobile phase consisted of 100:0 (v/v) buffer A:buffer B[Water-methanol-formic acid (500:500:1, v/v/v)] with gradient elution at flow rate of 0.4 mL/min. Elution was in linear gradient, where buffer B increased from 0% to 45% between 0.5 and 4 min, then increased to 60% at 4.01 min, maintained at 60% for 1 min, then decreased to 0% at 5.01 min, then maintained at 0% for 1 min. The Mass spectrometer was performed under the settings which selected electrospray ionization for Ionization method and positive for Ion polarity. Nitrogen was used as the Curtain gas (40 psi) and air was used as nebulizer gas (50 psi) and heaters gas (40 psi). Ion monitoring conditions were defined as Ion spray voltage of 4.5 kV and Turbo probe temperature of 600° C. These settings for declustering potential, entrance potential and collision energy were 110 V, 8V and 22 eV, respectively. Data was acquired by multiple reaction monitoring (MRM) using mass to charge ratio (m/z) 384→162 for HS, m/z 426→236 for DS, m/z 390→162 for HS-d6 and m/z 432→162 for DS-d6. Peak areas, STD curve, and measured concentrations were calculated with Analyst ver.1.5.1 (AB Scix).

Statistical Analysis

Statistical analysis was performed by GraphPad Prism 6. The MannWhitney U test was used to compare differences between each drug-treated group and vehicle-treated group in KO mice. Differences with P values less than 0.05 were considered statistically significant. Data were presented as means and SEM. To determine the relationship between CSF HS and brain HS and between CSF HS and brain GAGs, we evaluated 73 samples of mouse CSF and brain tissue, and data were analyzed using Spearman's rho and linear regression. Intraclass correlation coefficients (ICCs) and 95% confidence intervals were computed.

1-3: Results

Body Weights

The body weights of all experimental groups were not significantly changed during the study period. There were no significant differences in the weights of the mice in the ICV ERT groups compared with those in the control groups (WT and non-treated IDS KO mice). We also did not find any abnormal clinical signs during the experiments in any of the ERT groups.

Single ICV Injection of IDS-β Decreased GAGs in Brain Tissue of IDS KO Mice

The total GAGs in the brain tissue of the KO mice in the vehicle injection group were significantly higher compared to those of the WT mice (FIG. 1). The total GAGs in the brain tissue of all the IDS-β-treated groups were significantly reduced compared to those of the disease-control mice after 7 days of dosing (FIG. 1). However, re-accumulation of GAGs was observed 14 days after injection in the 3- and 10-μg injection groups. At 28 days after injection, the significant GAG reduction was maintained in the 30-μg injection group despite the total GAG level was slightly re-increased compared to that of day 7 and day 14 (FIG. 1).

Figure 2:
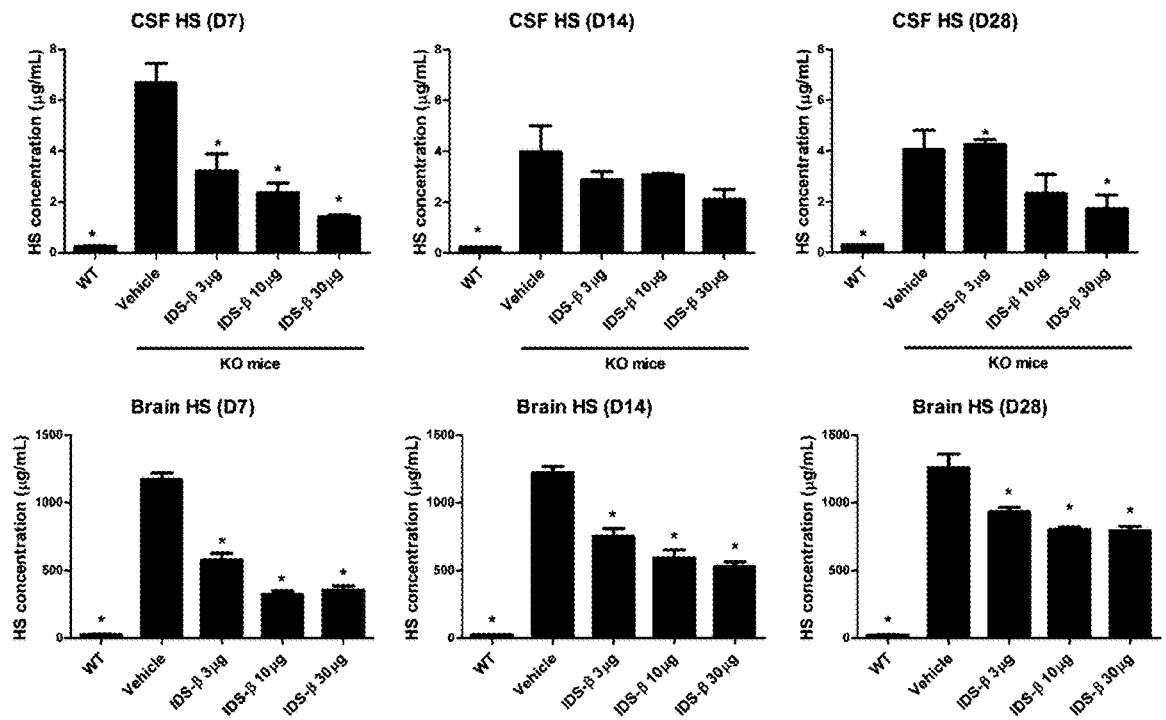
FIG. 2 shows HS levels in CSF and brain tissues of IDS KO mice after single ICV injection of IDS-γ.

Single ICV Injection of IDS-β Decreased HS in CSF and Brain Tissue of IDS KO Mice The HS level was significantly increased in the CSF and brain tissue of IDS KO mice compared to that of WT control mice (FIG. 2). At seven days after ICV injection, the HS content in the CSF and brain tissue was significantly decreased in all three IDS-β-treated groups. The significant reductions of HS in the brain tissue were maintained throughout the 28 days (FIG. 2). The HS content in the CSF remained decreased at 14 and 28 days after ICV injection. However, statistical significance was only found in the 30-μg IDS-β-treated group at 28 days after ICV injection (FIG. 2).

HS Content in CSF were Positively Correlated with Brain Tissue HS and GAGs

Figure 3A:
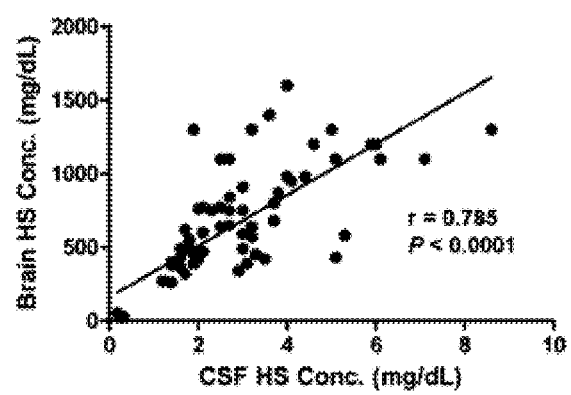
FIGS. 3(A) and 3(B) show a correlation between HS level in CSF and HS level in brain tissues of IDS KO mice after single ICV injection of IDS-β.
Figure 3B:
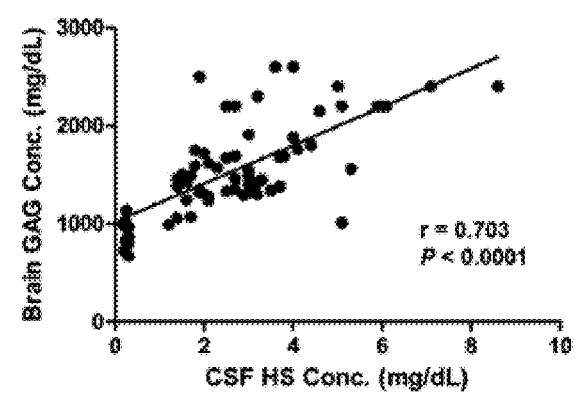

A significant positive correlation was found between HS content in the CSF and HS concentration in the brain tissue of mice samples (r=0.785, P<0.0001) (FIG. 3A). Furthermore, the HS content in the CSF also had a significant positive correlation with the GAG concentration of brain tissue (r=0.703, P<0.0001) (FIG. 3B).

Single ICV Injection of IDS-β Decreased GAGs of Somatic Tissues of IDS KO Mice

Figure 4:
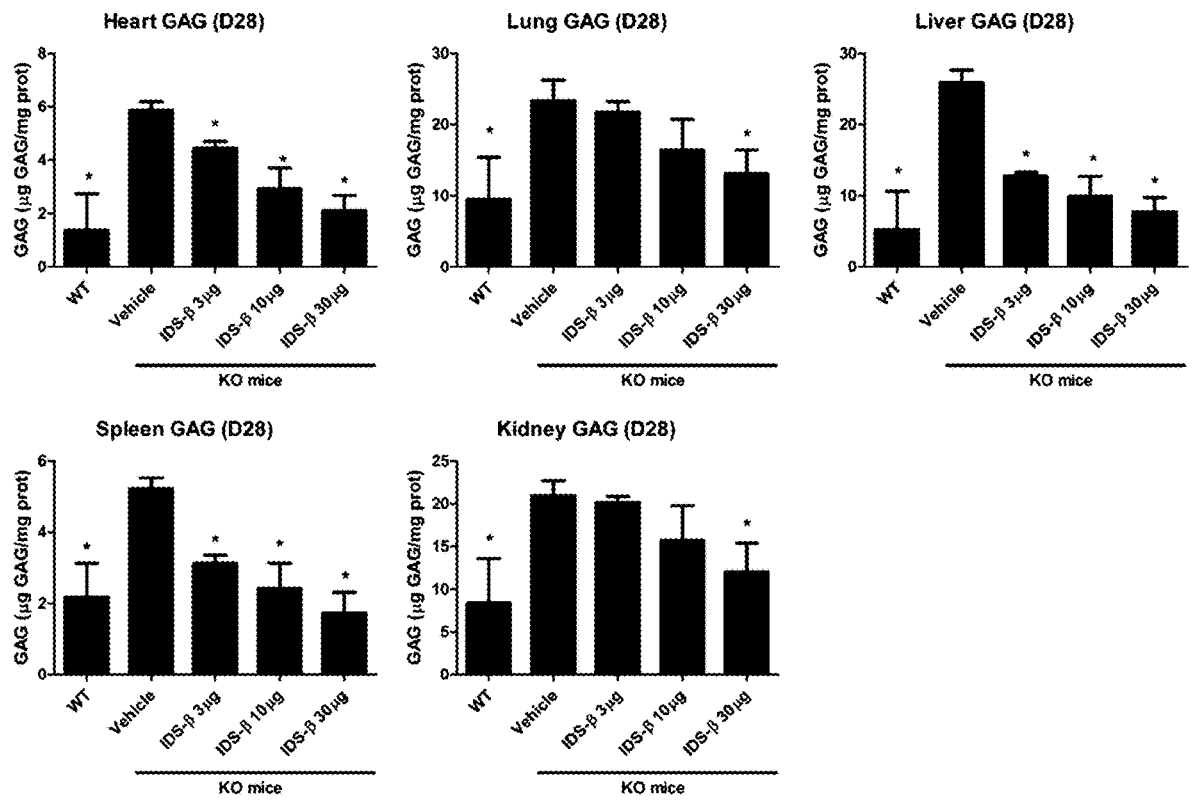
FIG. 4 shows GAGs levels in somatic tissues of IDS KO mice after single ICV injection of IDS-β.

We measured total GAG concentration following a single ICV injection in both brain tissue and other somatic tissues (heart, lung, liver, spleen, and kidney). The accumulation of GAGs was found in all analyzed tissues of the IDS KO mice with the vehicle injection compared to WT mice (FIG. 4). At 28 days after ICV injection, ICV administration with 30 μg of IDS-β maintained a significant reduction of total GAGs in all of the examined tissues (FIG. 4). The GAG concentrations of somatic tissues at 7 and 14 days after ICV injection are shown in FIG. 6-10.

1-4: Discussion

MPS II is the most common type of MPS in Asia, and approximately 70% of patients with MPS II have the severe form [18, 19]. Therefore, correction of the brain pathology is one of the most important and challenging issues in the treatment of patients with MPS II. Intrathecal or intraventricular injection of the recombinant enzyme has been suggested as a strategy to deliver the therapeutic drug into the brain. In this study, we performed single ICV injections of three different doses of IDS-β in 6-week-old IDS KO mice to evaluate the doseresponse relationship and the time course of the pharmacological effect.

The total GAGs in the brain tissue of all the IDS-β-treated groups were significantly reduced, and the significant GAG reduction was maintained for 28 days in the 30-μg injection group (FIG. 1). The significant reduction of CSF HS concentration was also consistently observed in the 30-μg-treated group at 28 days after ICV injection (FIG. 2). Therefore, we suggest that a 30-μg IDS-β injection into the lateral ventricle once every four weeks could be effective in the reduction and maintenance of accumulated brain GAGs in MPS II mice. Furthermore, these results could serve as basic evidence for deciding dose and injection frequency in the clinical use of ICV injections of the recombinant enzyme although the different size of brain and metabolic rate between mice and human should be considered. However, to further elucidate the efficacy of ICV enzyme administration for improving CNS pathology in MPS II, we need to expand the study with repeated injections and conduct functional assessments including behavioral tests and histological analyses of the brain.

Among the various types of MPS, CNS involvement is present in the severe form of MPS I (Hurler disease), the severe form of MPS II, MPS III, and MPS VII. In contrast, patients with MPS IV, MPS VI, the attenuated type of MPS I (Scheie syndrome), and the attenuated type of MPS II do not have cognitive impairment [2]. HS is one of the principal accumulating GAGs in MPS I, II, III, and VII [10]. Several reports have demonstrated that the accumulated HS in the brain tissue is responsible for the neurological manifestations of MPSs [9-12]. Furthermore, it has been shown that HS concentration is a more sensitive and specific biomarker in the brain tissue of MPS II mice [13, 20]. However, the direct measurement of the amount of HS in the brain tissue is impossible in the clinical setting. Therefore, we analyzed HS concentrations in the CSF and tried to find a correlation between HS level in the CSF and brain tissue. We demonstrated that HS content was significantly increased in both the CSF and brain tissue of IDS KO mice compared to WT mice and decreased in all IDS-β-treated groups (FIG. 2). Furthermore, this is the first study to demonstrate that the HS concentration in the CSF was significantly correlated with brain tissue HS and brain tissue GAGs (FIG. 3). Therefore, we suggest that HS content in the CSF could be one of the potential biomarker for assuming brain tissue HS levels or GAGs. However, for demonstrating HS content in CSF can really represent CNS pathology, we need additional study including pathologic exam of brain tissue because CNS pathology of MPS II are resulted from not only amount of GAG accumulation but also secondary substrate accumulation, inflammation, and degenerative changes of CNS [12, 21, 22]. If the correlation will be demonstrated, CSF HS content could be a useful parameter for assessing CNS pathology in possible future clinical trials of MPS II patients with CNS involvement.

Additionally, we demonstrated that the ICV administration of IDS-β also significantly reduced the GAG accumulation of somatic tissues (liver, spleen, kidney, heart, and lung) as well as brain tissue in a dose-dependent manner, although the effect differed among the tissues (FIG. 4 and FIG. 6-10). The degree of GAG reduction was observed to be dose dependent, and we noted that the administration of 30 μg of IDS-R could significantly reduce and maintain the accumulated GAGs in somatic tissues for 28 days, which was the same as in the brain tissue. Overall, these data demonstrate the physiological transport of a therapeutic protein from the CSF to the systemic organs after ICV administration, suggesting a clinically feasible route for the delivery of the therapeutic enzyme to both the brain and systemic organs. In addition, the CSF could serve as an intermediate reservoir for an injected enzyme from which some amounts are gradually transferred into the systemic circulation after ICV injection. Although the mechanism of enzyme delivery from the CSF to the systemic circulation is not clear, it has been suggested that the CSF containing iduronate-2-sulfatase might communicate with the systemic venous circulation via the subarachnoid space [6, 23-25].

In conclusion, a single ICV injection of IDS-β was well tolerated, and it produced a significant reduction of HS and GAGs in the brain tissue and GAGs in the somatic tissues of IDS KO mice. Moreover, the effect was maintained at 28 days after ICV injection, especially at the 30-μg dose. In addition, the CSF HS concentration could be a useful biomarker for representing brain pathology, because the CSF HS concentration was positively correlated with brain tissue HS and GAGs.

1-5: SEQUENCE LISTING
Length: 525
Type: PRT

SEQ ID NO: 1
SETQANSTTD ALNVLLIIVD DLRPSLGCYG DKLVRSPNID

QLASHSLLFQ NAFAQQAVCA PSRVSFLTGR RPDTTRLYDF

NSYWRVHAGN FSTIPQYFKE NGYVTMSVGK VFHPGISSNH

```
                      -continued
TDDSPYSWSF PPYHPSSEKY ENTKTCRGPD GELHANLLCP

VDVLDVPEGT LPDKQSTEQA IQLLEKMKTS ASPFFLAVGY

HKPHIPFRYP KEFQKLYPLE NITLAPDPEV PDGLPPVAYN

PWMDIRQRED VQALNISVPY GPIPVDFQRK IRQSYFASVS

YLDTQVGRLL SALDDLQLAN STIIAFTSDH GWALGEHGEW

AKYSNFDVAT HVPLIFYVPG RTASLPEAGE KLFPYLDPFD

SASQLMEPGR QSMDLVELVS LFPTLAGLAG LQVPPRCPVP

SFHVELCREG KNLLKHFRFR DLEEDPYLPG NPRELIAYSQ

YPRPSDIPQW NSDKPSLKDI KIMGYSIRTI DYRYTVWVGF

NPDEFLANFS DIHAGELYFV DSDPLQDHNM YNDSQGGDLF

QLLMP

Length: 525
Type: PRT
                                          SEQ ID NO: 2
SETQANSTTD ALNVLLIIVD DLRPSLGCYG DKLVRSPNID

QLASHSLLFQ NAFAQQAVG*A PSRVSFLTGR RPDTTRLYDF

NSYWRVHAGN FSTIPQYFKE NGYVTMSVGK VFHPGISSNH

TDDSPYSWSF PPYHPSSEKY ENTKTCRGPD GELHANLLCP

VDVLDVPEGT LPDKQSTEQA IQLLEKMKTS ASPFFLAVGY

HKPHIPFRYP KEFQKLYPLE NITLAPDPEV PDGLPPVAYN

PWMDIRQRED VQALNISVPY GPIPVDFQRK IRQSYFASVS

YLDTQVGRLL SALDDLQLAN STIIAFTSDH GWALGEHGEW

AKYSNFDVAT HVPLIFYVPG RTASLPEAGE KLFPYLDPFD

SASQLMEPGR QSMDLVELVS LFPTLAGLAG LQVPPRCPVP

SFHVELCREG KNLLKHFRFR DLEEDPYLPG NPRELIAYSQ

YPRPSDIPQW NSDKPSLKDI KIMGYSIRTI DYRYTVWVGF

NPDEFLANFS DIHAGELYFV DSDPLQDHNM YNDSQGGDLF

QLLMP
```

(The 59th amino acid "G*" of SEQ ID NO:2 stands for a Formyl-Glycine.)

1-6: References

[1] Bach G, Eisenberg F, Jr., Cantz M, Neufeld E F: The defect in the Hunter syndrome: deficiency of sulfoiduronate sulfatase. Proc Natl Acad Sci USA 1973, 70:2134-2138.

[2] Neufeld E F, Muenzer J. The mucopolysaccharidoses. In: Scriver C R, Beaudet A L, Sly W S, Valle D (eds). The Metabolic and Molecular Bases of Inherited Disease, vol. III. McGraw-Hill: New York, 2001:34213452.

[3] Kakkis E, McEntee M, Vogler C, Le S, Levy B, Belichenko P, Mobley W, Dickson P, Hanson S, Passage M: Intrathecal enzyme replacement therapy reduces lysosomal storage in the brain and meninges of the canine model of MPS I. Mol Genet Metab 2004, 83:163-174.

[4] Auclair D, Finnie J, White J, Nielsen T, Fuller M, Kakkis E, Cheng A, O'Neill C A, Hopwood J J: Repeated intrathecal injections of recombinant human 4-sulphatase remove dural storage in mature mucopolysaccharidosis VI cats primed with a short-course tolerisation regimen. Mol Genet Metab 2010, 99:132-141.

[5] Hemsley K M, Hopwood J J: Delivery of recombinant proteins via the cerebrospinal fluid as a therapy option for neurodegenerative lysosomal storage diseases. Int J Clin Pharmacol Ther 2009, 47 Suppl 1:S118-123.

[6] Higuchi T, Shimizu H, Fukuda T, Kawagoe S, Matsumoto J, Shimada Y, Kobayashi H, Ida H, Ohashi T, Morimoto H et al: Enzyme replacement therapy (ERT) procedure for mucopolysaccharidosis type II (MPS II) by intraventricular administration (IVA) in murine MPS II. Mol Genet Metab 2012, 107:122-128.

[7] Calias P, Papisov M, Pan J, Savioli N, Belov V, Huang Y, Lotterhand J, Alessandrini M, Liu N, Fischman A J et al: CNS penetration of intrathecal-lumbar idursulfase in the monkey, dog and mouse: implications for neurological outcomes of lysosomal storage disorder. PLoS One 2012, 7:e30341.

[8] Muenzer J, Hendriksz C J, Fan Z, Vijayaraghavan S, Perry V, Santra S, Solanki G A, Mascelli M A, Pan L, Wang N et al: A phase I/II study of intrathecal idursulfase-IT in children with severe mucopolysaccharidosis II. Genet Med 2015.

[9] de Ruijter J, Ijlst L, Kulik W, van Lenthe H, Wagemans T, van Vlies N, Wijburg F A: Heparan sulfate derived disaccharides in plasma and total urinary excretion of glycosaminoglycans correlate with disease severity in Sanfilippo disease. J Inherit Metab Dis 2013, 36:271-279.

[10] Coppa G V, Gabrielli O, Zampini L, Maccari F, Mantovani V, Galeazzi T, Santoro L, Padella L, Marchesiello R L, Galeotti F et al: Mental retardation in mucopolysaccharidoses correlates with high molecular weight urinary heparan sulphate derived glucosamine. Metab Brain Dis 2015, 30:1343-1348.

[11] Bruyere J, Roy E, Ausseil J, Lemonnier T, Teyre G, Bohl D, Etienne-Manneville S, Lortat-Jacob H, Heard J M, Vitry S: Heparan sulfate saccharides modify focal adhesions: implication in mucopolysaccharidosis neuropathophysiology. J Mol Biol 2015, 427:775-791.

[12] Wilkinson F L, Holley R J, Langford-Smith K J, Badrinath S, Liao A, Langford-Smith A, Cooper J D, Jones S A, Wraith J E, Wynn R F et al: Neuropathology in mouse models of mucopolysaccharidosis type I, IIIA and IIIB. PLoS One 2012, 7:e35787.

[13] Akiyama K, Shimada Y, Higuchi T, Ohtsu M, Nakauchi H, Kobayashi H, Fukuda T, Ida H, Eto Y, Crawford B E et al: Enzyme augmentation therapy enhances the therapeutic efficacy of bone marrow transplantation in mucopolysaccharidosis type II mice. Mol Genet Metab 2014, 111:139-146.

[14] Lawrence R, Brown J R, Al-Mafraji K, Lamanna W C, Beitel J R, Boons G J, Esko J D, Crawford B E: Disease-specific non-reducing end carbohydrate biomarkers for mucopolysaccharidoses. Nat Chem Biol 2012, 8:197-204.

[15] Jung S C, Park E S, Choi E N, Kim C H, Kim S J, Jin D K: Characterization of a novel mucopolysaccharidosis type II mouse model and recombinant AAV2/8 vector-mediated gene therapy. Mol Cells 2010, 30:13-18.

[16] Lee W C, Tsoi Y K, Troendle F J, DeLucia M W, Ahmed Z, Dicky C A, Dickson D W, Eckman C B: Single-dose intracerebroventricular administration of galactocerebrosidase improves survival in a mouse model of globoid cell leukodystrophy. Faseb j 2007, 21:2520-2527.

[17] Glascock J J, Osman E Y, Coady T H, Rose F F, Shababi M, Lorson C L: Delivery of therapeutic agents through intracerebroventricular (ICV) and intravenous (IV) injection in mice. J Vis Exp 2011.

[18] Lin H Y, Lin S P, Chuang C K, Niu D M, Chen M R, Tsai F J, Chao M C, Chiu P C, Lin S J, Tsai L P et al:

Incidence of the mucopolysaccharidoses in Taiwan, 1984-2004. Am J Med Genet A 2009, 149A:960-964.

[19] Sohn Y B, Choi E W, Kim S J, Park S W, Kim S H, Cho S Y, Jeong S I, Huh J, Kang I S, Lee H J et al: Retrospective analysis of the clinical manifestations and survival of Korean patients with mucopolysaccharidosis type II: emphasis on the cardiovascular complication and mortality cases. Am J Med Genet A 2012, 158A:90-96.

[20] Shimada Y, Wakabayashi T, Akiyama K, Hoshina H, Higuchi T, Kobayashi H, Eto Y, Ida H, Ohashi T: A method for measuring disease-specific iduronic acid from the non-reducing end of glycosaminoglycan in mucopolysaccharidosis type II mice. Mol Genet Metab 2015.

[21] Hamano K, Hayashi M, Shioda K, Fukatsu R, Mizutani S: Mechanisms of neurodegeneration in mucopolysaccharidoses II and IIIB: analysis of human brain tissue. Acta Neuropathol 2008, 115:547-559.

[22] Archer L D, Langford-Smith K J, Bigger B W, Fildes J E: Mucopolysaccharide diseases: a complex interplay between neuroinflammation, microglial activation and adaptive immunity. J Inherit Metab Dis 2014, 37:1-12.

[23] Chen L, Elias G, Yostos M P, Stimec B, Fasel J, Murphy K: Pathways of cerebrospinal fluid outflow: a deeper understanding of resorption. Neuroradiology 2015, 57:139-147.

[24] Hladky S B, Barrand M A: Mechanisms of fluid movement into, through and out of the brain: evaluation of the evidence. Fluids Barriers CNS 2014, 11:26.

[25] Glimcher S A, Holman D W, Lubow M, Grzybowski D M: Ex vivo model of cerebrospinal fluid outflow across human arachnoid granulations. Invest Ophthalmol Vis Sci 2008, 49:4721-4728.

The invention claimed is:

1. A method of treating Hunter Syndrome comprising a step of administering intracerebroventricularly (ICV administration) to a subject in need of treatment a therapeutically effective dose of an ICV formulation comprising idursulfase-beta (IDS-β) protein at a concentration ranging from approximately 0.1 mg/ml to approximately 60 mg/ml, sodium chloride at a concentration of approximately 150 mM, polysorbate 20 at a concentration of approximately 0.05 mg/ml, and a pH of approximately 6,
wherein said ICV administration is through an intraventricular catheter system comprising a reservoir and a catheter connected to said reservoir.

2. The method of claim 1, wherein said ICV formulation comprises idursulfase-beta (IDS-β) protein at a concentration of approximately 15 mg/ml, Sodium chloride at a concentration of approximately 150 mM, polysorbate 20 at a concentration of approximately 0.05 mg/ml, and a pH of approximately 6.

3. The method of claim 1, wherein said therapeutically effective dose is ranging from approximately 1 mg to approximately 30 mg.

4. The method of claim 1, wherein said therapeutically effective dose is approximately 10 mg.

5. The method of claim 1, wherein said ICV administration is performed once every three weeks.

6. The method of claim 1, wherein said ICV administration is performed once every month.

7. The method of claim 1, further comprising steps of surgically implanting said intraventricular catheter system, wherein said reservoir is placed between the scalp and the brain of the subject in need of treatment and the end of said catheter is placed inside the ventricle of said subject such that the inner space of said reservoir is connected to the inner space of said ventricle through the inner space of said catheter so that cerebrospinal fluid flows from said ventricle into said reservoir to fill said reservoir;
drawing out 0.1-5 ml of cerebrospinal fluid from said reservoir at a flow rate of 0.1-60 ml/minute;
injecting 0.1-5 ml of said ICV formulation into said reservoir at a flow rate of 0.1-60 ml/minute; and
allowing said ICV formulation to flow from said reservoir through said catheter into said ventricle.

8. The method of claim 1, wherein said ICV administration is performed in combination with at least one additional route of administration of enzyme replacement therapy treatment for Hunter Syndrome.

9. The method of claim 8, wherein said additional route of administration of enzyme replacement therapy treatment for Hunter Syndrome is selected from the group consisting of intravenous administration and subcutaneous administration.

10. The method of claim 9, wherein said additional route of administration is intravenous administration; and wherein said ICV administration is performed once every month and said intravenous administration is performed once every week.

11. The method of claim 9, wherein said additional route of administration is intravenous administration; and wherein said ICV administration is performed once every three weeks and said intravenous administration is performed once every week.

12. The method of claim 9, wherein said additional route of administration is subcutaneous administration; and wherein said ICV administration is performed once every month and said subcutaneous administration is performed once every week.

13. The method of claim 9, wherein said additional route of administration is subcutaneous administration; and wherein said ICV administration is performed once every three weeks and said subcutaneous administration is performed once every week.

14. The method of claim 9, wherein said additional route of administration is subcutaneous administration; and wherein said ICV administration is performed once every month and said subcutaneous administration is performed twice every week.

15. The method of claim 9, wherein said additional route of administration is subcutaneous administration; and wherein said ICV administration is performed once every three weeks and said subcutaneous administration is performed twice every week.

16. The method of claim 9, wherein said additional route of administration comprises intravenous administration and subcutaneous administration; and
wherein said ICV administration is performed once every month and said intravenous administration and said subcutaneous administration are performed alternatively at an interval of one week.

17. The method of claim 9, wherein said additional route of administration comprises intravenous administration and subcutaneous administration; and wherein said ICV administration is performed once every three weeks and said intravenous administration and said subcutaneous administration are performed alternatively at an interval of one week.

* * * * *